(12) United States Patent
Chen

(10) Patent No.: US 6,645,508 B1
(45) Date of Patent: Nov. 11, 2003

(54) STABLE L-ASCORBIC ACID COMPOSITION

(76) Inventor: Jivn-Ren Chen, 7614 Brookhaven, Shreveport, LA (US) 71105

( * ) Notice: Subject to any disclaimer, the term of this patent is extended or adjusted under 35 U.S.C. 154(b) by 0 days.

(21) Appl. No.: 09/336,193

(22) Filed: Jun. 18, 1999

(51) Int. Cl.$^7$ ............. A01N 43/36; A61K 7/48; A61K 31/375

(52) U.S. Cl. ............. 424/401; 424/400; 514/152; 514/39; 514/474; 514/937; 514/944

(58) Field of Search ............. 514/152, 39, 474, 514/937, 944

(56) References Cited

U.S. PATENT DOCUMENTS

| | | |
|---|---|---|
| 3,969,516 A | 7/1976 | Stoughton |
| 4,132,781 A | 1/1979 | Stoughton |
| 4,376,118 A | 3/1983 | Daher et al. |
| 4,983,382 A | 1/1991 | Wilmott et al. |
| 5,670,142 A | 9/1997 | Rubin |
| 5,750,123 A * | 5/1998 | Znaiden et al. ............. 424/401 |
| 5,935,967 A * | 8/1999 | Hausheer et al. ........... 514/283 |
| 5,955,057 A * | 9/1999 | Maunder et al. ............. 424/44 |
| 6,020,367 A * | 2/2000 | Duffy et al. ................. 514/474 |

OTHER PUBLICATIONS

European Patent Office, International Search Report (PCT/US00/16755), Oct. 11, 2000.
Database WPI, Week 197825, Derwent Publications Ltd., AN 1978–44934A, XP002148800 & JP 53 052633 A (Sunstar Hamigaki K.), May 13, 1978, abstract.
Database WPI, Week 199246, Derwent Publications Ltd., AN 1992–376254, XP002148801 & JP 04 275206 A (Easai Co. Ltd.), Sep. 30, 1992, abstract.
U.S. Patent and Trademark Office, Written Opinion (PCT/US00/16755), Jun. 19, 2001.
U.S. Patent and Trademark Office, International Preliminary Examination Report (PCT/US00/16755), Nov. 1, 2001.

* cited by examiner

Primary Examiner—Russell Travers
Assistant Examiner—Shahnam J Sharareh
(74) Attorney, Agent, or Firm—Jackson Walker L.L.P.

(57) ABSTRACT

A stable composition including a water-sensitive pharmacologically active agent, such as an enzyme, an antibiotic or a vitamin, a hydrophilic non-polar primary solvent, an optional hydrophilic non-polar secondary solvent and optional pharmaceutical or cosmetic adjuvants to enhance appearance for topical use. Where the water-sensitive or water-degradable component is L-Ascorbic acid and the principal solvent is N-methyl-2-pyrrolidone ("NMP") the composition is stable for many months at a concentration of L-Ascorbic acid of up to about 40 % w/v. This composition using NMP as a solvent and enhancer of skin penetration together with appropriate adjuvants is useful for preparing dermatological topical dosage for cosmetic and therapeutic purposes.

8 Claims, No Drawings

STABLE L-ASCORBIC ACID COMPOSITION

BACKGROUND

The present invention relates to a composition containing a relatively high concentration of a water-sensitive pharmacologically active agent, such as L-Ascorbic acid, which composition is stable in this preparation for a commercially feasible time period and can be used, in particular, for topical cosmetic or medical therapeutic purposes to cleanse, care for, improve, or protect human tissue and skin.

The dermatological benefit of topical application of L-Ascorbic acid has been well established. A stable, skin-penetrable, high concentration composition of L-Ascorbic acid is needed for cosmetic and therapeutic purposes. Scientists have had difficulty for a long time formulating stable solutions of L-Ascorbic acid of high enough concentration which would be beneficial for cosmetic or dermatologic needs.

Although L-Ascorbic acid is more stable in some water-miscible organic solvents than in water itself, unfortunately its solubility in such non-aqueous media is very limited which prevents achieving a suitable concentration in an anhydrous medium. The desired level of stability and skin penetrability and therefore, efficacy are not attained. For this reason, presently unstable L-Ascorbic acid preparations have been used for cosmetic and therapeutic purposes at unsuitably low concentrations.

L-Ascorbic acid, $C_6H_8O_6$, molecular weight 176.1, commonly known as Vitamin C or ascorbic acid, is an unsaturated lactone or cyclic ester. It is unstable and reversibly oxidized to give biologically active dehydroascorbic acid in aqueous solution. The oxidation rate is dependent on pH and on oxygen concentration and is catalyzed by metal ions, especially Cu (II) and Fe (III). Dehydroascorbic acid quickly undergoes irreversible degradation to biologically inactive diketogulonic acid and oxalic acid. Oxidation is also subject to buffer catalysis by both general acids and general bases. A three-fold rise in rate is observed in 0.5 M phosphate buffer even in the pH range 1 to 4. The decomposition rate increases with various buffers and depends upon concentration. At neutral or higher pH of a typical cosmetic formulation, L-Ascorbic acid becomes the notoriously unstable ascorbate anion.

Optimum stability of ascorbic acid solution occurs around pH 2.5 to 3.0 (K. A. Connors, G. L. Amidon and L. Kennon, Chemical Stability of Pharmaceuticals, John Wiley & Sons, 1979). B. R. Hajratwala published a paper entitled "Stability of ascorbic acid" in the Revue sciences Pharmaceutiques on Mar. 15, 1985 and observed stabilization of ascorbic acid in acidic aqueous solution after addition of a surface-active agent and a chelating agent, with packaging under nitrogen in the absence of light. Moreover the hydroalcoholic solution in the patent having a pH lower than 3.5 may produce side effects such as irritation or burning of the skin. In this preparation ascorbic acid is insufficiently stabilized for commercial purposes.

Ascorbic acid is also susceptible to dehydration degradation under anaerobic conditions, giving furfural and carbon dioxide. The pH-decomposition rate profiles for both aerobic and anaerobic degradation show maxima about pH 4 near to its $pK_1$. Optimum stability occurs around pH 2.5 to 3.0 and pH 6.0 to 6.5. The catalytic degradation of ascorbic acid solution is particularly effective at lower pH values and can promote oxidation even in the absence of air. Catalysis by various other metal ions, such as Pb(II), Zn(II), and Al(III) has also been reported (P. Finholt et. al., J. Pharm. Sci. 55: 1435, 1966).

Although ascorbic acid is relatively soluble in aqueous media, it oxidizes rapidly in solution. On the other hand, ascorbic acid is relatively insoluble in organic solvents such as alcohol, glycol, fats, fat solvents and oils. Using high concentration of water miscible organic solvent, even in a co-solvent system, achieving a cosmetical and therapeutically desired concentration of ascorbic acid solution is difficult. Among pharmaceutical vehicles sorbitol, glycerin and propylene glycol can maintain about 90% potency of low concentration (about 1 to 10%) of ascorbic acid for one year, however this is still a short-term stabilization for commercial purposes.

The initial concentration of ascorbic acid in solution plays a key role in determining the rate of decomposition. It is reported that high concentrations, up to 5%–10%, show slightly better stability of ascorbic acid in water, propylene glycol or Syrup USP at room temperature.

U.S. Pat. No. 4,983,382 describes a stable composition of ascorbic acid for application to human skin as a cosmetic preparation. The preparation contains about 1 to 10% of ascorbic acid by weight, co-solvent of no more than 12% of water and water miscible organic solvents, emollients, fragrances, antioxidants and preservatives, or mixtures of the same. It specified a group of the alcohols, glycols, and polyols or mixtures thereof as second co-solvent comprising up to but no more than about 90% of the total weight of the composition in which propylene glycol is present in an amount by weight ranging from about 20% to 25% and ethanol is present in an amount by weight ranging from about 55% to 65%.

Kassem, et al. (M. A. Kassem et. al., Pharm. Acta Helv. 44: 611, 1969 and 47: 89, 1972) studied the effect of complexing agents and autoclaving of injectable ascorbic acid solutions. The stabilizing effectiveness of all metal complexing agents studied was limited.

Blaug and Hajratwala (S. M. Blaug et. al., J. Pharm. Sci. 63: 1240, 1974) observed an increase in aerobic oxidation rate of ascorbic acid with both surfactant, polysorbate 80, and polyoxalkol at low concentration of surfactant. At higher concentration, no change in rate was observed for polysorbate 80 but a 30% decrease in rate occurred for polyoxalkol.

Nixon and Chawla (J. R. Nixon et. al., J. Pharm. Pharmacol. 17: 558, 1965), using polysorbate 20, found an increase in decomposition rate with increasing viscosity at high concentration of surfactant. However, for the metal-catalyzed reaction, the rate decreased by a factor of 6 at about 70% w/w of polysorbate 20. The rate of copper-catalysed decomposition in the presence of polysorbate 80 has been found to decrease up to a concentration of 30% w/w polysorbate 80 in a study by Poust and Colaizzi (R. I. Poust et. al., J. Pharm. Sci. 57: 2119, 1968).

A monograph prepared by D. Madey (The Science Supporting Topical Vitamin C (L-Ascorbic Acid Products, no other publication information) also recognized that it is notoriously difficult to stabilize L-Ascorbic acid and it tends to break down rapidly. Instability restricts the only form of vitamin C body can use and its application to cosmetic preparations. The monograph also elaborates U.S. Pat. No. 5,140,043 ("the '043 Patent") which teaches a stable L-Ascorbic acid formulation in an initial laboratory preparation at pH 3.5. The '043 Patent describes a stable topical composition consisting essentially of at least about 1% to up to about 20% L-Ascorbic acid (w/v) in 80% to 97% water and a carrier such as propylene glycol or combination of propylene glycol and hydroxypropylcellulose. This aqueous preparation with pH of 2.5 to 3.5 can be applied to the skin as a method of preventing, treating and retarding damage to skin by ultraviolet light.

A stable composition for topical application in U.S. Pat. No. 5,703,041 ("the '041 Patent") contains at least 0.001 to 15% of one water-degradable active agent with a topical action including ascorbic acid, at least 30 to 99.9% by weight of one polyol, such as, glycerol or propylene glycol, and at least one structuring agent, such as glyceryl polyacrylate polymer and/or oil, such as mineral oil and water. The water-sensitive active agent can also be an enzyme. The composition obtained can be used for cleansing, caring for or protecting skin or keratinous fibers. A stabilized form of L-Ascorbic acid at low pH for cosmetic use has been marketed recently by SkinCeuticals (Dallas, Tex.).

Several stabilized derivatives, esters, and analogs of ascorbic acid in cream, such as ascorbyl palmitate, magnesium ascorbyl phosphate, ascorbyl methyl silanol and other ester salts have been selected to stabilize the acid. Unfortunately these derivatives must get into skin and then be converted to L-Ascorbic acid by available cellular enzymes, a largely inefficient process. Presently there is no evidence that ascorbic acid derivatives, ester and analogs can directly enter the skin. It would be predicted also that salts such as ascorbic acid sulphate and ascorbic acid magnesium phosphate would not enter because of their charged nature.

Two studies indicate that vitamin C derivatives do not perform in the same way as topical L-Ascorbic acid. Kameyama et al. (Kameyama K. et al., J. Am. Acad. Dermatol. 34: 29–33, 1996) show that percutaneous absorption of magnesium ascorbyl 2-phosphate is low, less than 2%. It may not be absorbed or not converted to L-Ascorbic acid in high enough concentrations on the skin to have pharmacological activity. Furthermore esters of ascorbic acid such as ascorbyl stearate or ascorbyl palmitate might chemically prefer the environment of a cream to that of the skin and therefore not substantially enter skin. Ascorbyl palmitate and L-Ascorbic acid were shown to stimulate collagen synthesis equally in a dose-dependent manner. Comparison research revealed ascorbyl palmitate killed human skin fibroblasts at equivalent concentrations by an unknown mechanism (Murad S. et al., unpublished observation, 1997).

U.S. Pat. No. 5,516,793 describes a method for reducing irritation induced by topical application of a dermatological agent comprising a composition containing 0.5% to about 25% by weight of ascorbic acid or its derivatives in a cosmetically and pharmaceutically acceptable vehicle. This composition can be topically applied as a separate solution or by admixture with a cosmetically or pharmaceutically acceptable vehicle for the topically active dermatological agent including alpha-hydroxy acids, beta-hydroxy acids, keto acids, benzoyl peroxide, retinol (Vitamin A), retinoic acid, retinal, Vitamin $A_2$, Vitamin A epoxide, lactamides and quaternary ammonium lactate, $C_4$–$C_{12}$ hydroxylated carboxylic acids, sulfur, resorcinol and salicylic acid and various derivatives thereof to decrease skin irritation caused by the topical administration of these active ingredient(s). This composition contains water, alcohol and polyol. The stability of ascorbic acid in the preparation was not discussed.

U.S. Pat. No. 5,703,122 describes a dermatological composition including 0.5% to about 25% by weight of ascorbic acid or its derivatives in a cosmetically or pharmaceutically acceptable vehicle selected from the group consisting of water, propylene glycol, ethanol, propanol, glycerine, polyvinyl alcohol, and mixtures thereof with at least one adjuvant. This composition can be topically applied as a separate solution or by admixture with a cosmetically or pharmaceutically acceptable vehicle for active ingredient such as alpha-hydroxy acids, beta-hydroxy acids, keto acids, benzoyl peroxide, retinol (Vitamin A), retinoic acid, retinal $A_2$, Vitamin A epoxide, lactamides and quaternary ammonium lactate, $C_4$–$C_{12}$ hydroxylated carboxylic acids, sulfur, resorcinol, and salicylic acid and various derivative thereof to decrease skin irritation caused by the topical administration of these active ingredient(s). This patent uses a mixture of water, polyols, alcohol and polyvinyl alcohol as a vehicle for ascorbic acid. Stability of the active ingredient is not discussed.

U.S. Pat. No. 4,818,521 describes a stable oil-water emulsion containing L-Ascorbic acid in an oil emulsified with a non-ionic surface active fatty acid ester and other conventional ingredients for a cosmetic emulsion. It taught an art of stabilization of ascorbic acid in an oil-water emulsion cosmetic not a clear solution.

U.S. Pat. No. 4,938,969 teaches a method of treatment to reduce the depth or intensity of fine wrinkles in skin affected by intrinsic or photo-induced aging by applying a composition consisting of about 2% to about 20% of ascorbic acid, about 1% to 10% tyrosine, and about 0.5% to about 5% zinc sulfate in a hydrophilic ointment or cream base. There was no mention of stability of ascorbic acid in this carrier.

U.S. Pat. No. 5,322,683 discloses an anhydrous topically applicable aerosol foam composition comprising a foamable anhydrous liquid, a foaming agent and a propellant. The purpose of this invention apparently is to provide an anhydrous and hydrophobic topically applicable aerosol foam possessing cosmetic advantages such as production of a stable measurable foam which is resistant to washing off during swimming rather than to promote stability of an active ingredient in the preparation.

U.S. Pat. No. 5,736,567 discloses a stable water-in-oil emulsion for topical application which contains 0.05 to 10% by weight of ascorbic acid dissolved in at least 14% by weight of water and at least one polyol, i.e. glycerol or/and glycols, at least one structuring agent chosen from polymers and oils comprising 5 to 50% by weight of oil, at least one dispersant, at least 0.1 to 30% of an inorganic salt, and at least one lipophilic or hydrophilic adjuvant. The stabilizing effect on ascorbic acid in this composition persists over the course of time. The emulsion so obtained can be employed for treating or caring for the skin. The significant amount of water is used in this emulsion and the stability of ascorbic acid in the aqueous phase may be noteworthy.

N-Methyl-2-pyrrolidone ("NMP") is a stable liquid with well defined physical, chemical, solubilizing, and toxicity properties. High quality Good Manufacture Practice ("GMP") grade material can be specifically used in pharmaceutical and cosmetical products. NMP is exceedingly resistant to hydrolysis except at a pH below 1.5 or above 11.0. At high relative humidity, above 80%, weight gain due to hydration is rapid and continues for an extended time period. At lower humidities, the absorption of water is slower and peaks at a composition approximating the trihydrate molecule. After reaching this composition, there is a gradual loss of weight because of the evaporation of NMP. Eventually, the rate of absorption of water gradually decreases and the loss by volatilization of NMP is more substantial. The viscosity of a mixture of water and NMP increases up to about 30% water and decreases with the continued addition of water. The pyrrolidone ring on the NMP molecular structure undergoes a large number of chemical reactions. Enhanced solubility of certain drugs can possibly be attributed to a complexing reaction with the nitrogen and carbonyl reactive centers of that ring. Solubility enhancement can be attributed to three parameters: Nonpolar molecular dispersion; polar type chemical bonding; and hydrogen bonding.

NMP has been compared with the commonly used solvent Dimethyl sulfoxide (DADO) using the Hansen Solubility Parameters (CRC Handbook of Solubility Parameters and Other Cohesion Parameters, A. F. M. Barton, CRC Press, Boca Raton, Fla., 153–7, 1983). The Total Solubility Parameter of several commonly used solvents is listed as following for comparison:

| Solvent | Total Solubility Parameter |
| --- | --- |
| NMP | 11.2 |
| DMSO | 13.0 |
| Cyclohexanone | 9.6 |
| Methyl chloride | 9.9 |

NMP is a strong proton acceptor and forms complexes with many hydrogen donors such as ascorbic acid and water. NMP strongly binds two molecules of water, presumably to the carbonyl group, while a third molecule is lightly bonded, perhaps to nitrogen (P. Assarson et. al., ACS Symp. Ser. 9 (Colloidal Dispersions Micellar Behav., Pap. Symp., 1974, 288, 1975).

Percutaneous drug penetration enhancers have been described in several papers (M. Hori et. al., J. Pharm. Pharmacol. 42: 71, 1989) and B. W. Barry, Dermatological Formulations, Percutaneous Absorption, Marcel Dekker, N.Y., 160, 1983). The skin permeation of two non-steroidal inflammatory drugs (ibuprofen and flubiprofen) in a transdermal pad has been enhanced by the addition of NMP (S. A. Akhteret. al.,J. Pharma. Pharmacol. 37: 27,1984). The addition of NMP in different ointment formulations of mefenamic acid has been reported to increase skin penetration of the drug (S.I. Naito et. al., Int. J. Pharmaceutics 24: 127, 1985).

It is also reported (B. W. Barry et. al., J. Invest. Derm. 82: 49, 1984) that only NMP of all skin penetrant enhancers studied significantly increased the bioavailability of betamethasone 17-benzoate. Another study on the bioavailability of topical steroids demonstrated that NMP established superior stratum corneum reservoirs to other penetration enhancers (D. Southwell et.al., Intl. J. Pharmaceutics 18: 299, 1984).

U.S. Pat. No. 3,969,516 teaches that the topically application of antibiotic lincomycin cream or lotion containing NMP is an effective treatment for acne preferred over the systemic use of antibiotics.

Eur. Pat. Appl. 83300482.3 claimed the use of NMP to help solubilize the active ingredients 2-hydroxyoctanoic acid or 2-ketooctanoic acid for the topical treatment of acne. The poor water solubility of triethylenetetramine ("trien") and zinc pyrithione often produces a cloudy suspension in formulating products and causes a problem in the treatment of acne. By incorporating certain percentage of NMP in the finished product, pharmaceutically acceptable gels, ointments and lotions can be obtained.

The use of NMP as a solubilizer in topical dosage forms can improve the release rate of salicylic acid and indomethacin from a hydrophilic petrolatum ointment by lowering the affinity of the drug to the base (M. Shiozaki et. al., Yakuzaigaku 42: 10, 1982).

U.S. Pat. No. 3,932,653 lists several topical formulas in which NMP solubilizes griseofulvin for the treatment of fungal infections in both humans and animals.

The invention of U.S. Pat. No. 3,957,994 describes the use of theophylline as a topical anti-inflammatory active ingredient and discusses novel active compositions comprising NMP. The test result in this patent concludes theophylline is an effective anti-inflammatory agent in the presence of NMP but is ineffective in its absence.

U.S. Pat. No. 4,278,684 demonstrates that the systemic antihelmintic effect of levaminsole and tetraminsole on animals when applied topically can be improved by using NMP to promote drug penetration through the skin.

UK Patent Application GB2000970A claims the addition of povidone (Plasdone K-29/32) to chloramphenicol in NMP injectable solution can eliminate pain and irritation problems in treated animals. Povidone, with a molecular weight between 5,000 to 100,000 (Plasdone C-15 to C-30), presented as a co-solubilizer in NMP aqueous base injectable may also improve tissue toleration in the injected animals.

Up to present, there has been no reported use of NMP as a hydrophilic non-polar solvent to solubilize and stabilize ascorbic acid for topical application.

Dimethyl isosorbide ("DMI"), which has empirical formula $C_8H_4O_4$, is chemically defined as a 1,4:3,6 dianhydro 2,5-di-O-methyl-D-glucitol. Under the commercial trade name Arasolve, DMI is marketed by ICI (Wilmington, Del.), also available from Aldride Chemical Company (St. Louis, Mo.). It is a unique solvent for both pharmaceutical and cosmetic applications because of the following special characteristics advantages:

excellent solvent properties for many water insoluble active pharmaceutical ingredients may be used either as a low viscosity pure solvent, a co-solvent, or as carrier, in gel, cream and lotion formulae miscibility in all proportions with water and soluble in oil.

DMI has found valuable use in personal care formulations because of its unique solvent power. Since it is a colorless, practically odorless liquid with a dry feel, it can be beneficially used to dissolve various active ingredients incorporated into a cosmetic preparation. DMI can easily be thickened with cellulosic substances to readily form a sparkling clear, anhydrous, non-volatile, water-soluble gel; the consistency of the gel can be varied from soft, custard-like viscosity to a rigid gel depending upon the amount of cellulose used. There is no disclosures of this hydrophilic non-polar solvent being used to solubilize and stabilize ascorbic acid for topical application.

There are many attempts to develop and market an acceptable cosmetic and therapeutic formulation containing stable and efficacious concentrations of a water-sensitive pharmacologically active agent, such as ascorbic acid. This goal has not yet been achieved as indicated by published results and by market product searching.

SUMMARY

A hydrophilic non-polar solvent is used as a primary solvent not only to dissolve a relatively high concentration of a water-sensitive pharmacologically active agent, such as L-Ascorbic acid, but also to enhance the skin penetration of this active ingredient. L-Ascorbic acid can be made up to 40% weight by volume (w/v) solution to constitute a major part of a stable composition for topical application to gain dermatological effectiveness. The hydrophilic non-polar primary solvent used in this invention can be N-alkylpyrrolidones. A secondary solvent may also be included in the composition and may be selected from the group consisting of dimethyl isosorbide or polyol. The composition also can contain at least one dermatologically acceptable polymer and other pharmaceutical or cosmetic adjuvants.

DETAILED DESCRIPTION

In one aspect, the present invention relates to a stable composition containing at least one water-sensitive pharmacologically active ingredient and at least one hydrophilic non-polar solvent. The composition may also contain at least one secondary solvent, dermatological polymer and other pharmaceutical or cosmetic adjuvants.

One important aspect of this invention relates to a relatively high concentration of at least one water-sensitive pharmacologically active ingredient solubilized and stabilized in at least one hydrophilic non-polar liquid as a primary solvent and skin penetration enhancer. The concentration of the primary solvent ranges from about 30 to about 95% by volume of the total composition. The composition also can contain at least one secondary solvent, a dermatologically acceptable polymer and other pharmaceutical or cosmetic adjuvants. The concentration of water-sensitive L-Ascorbic acid, for example in the invention can be as high as 40% by weight in the composition. Such a high concentration is difficult to attain even in water, the best known solvent for L-Ascorbic acid.

An ascorbic acid topical composition containing polyols is known, but it has never been shown that a critical concentration of polyol can reach a desirable high concentration of ascorbic acid and prevent the degradation of ascorbic acid. The '043 Patent has emphasized that the ratio of water to polyols is at least 1:1.

The '401 Patent describes that in the case of topical compositions, polyols used in a sufficient quantity and in combination with a structuring agent are able to prevent degradation of water-sensitive active agents. This invention uses polyols as a major solvent.

As discussed above, the more stable derivatives, such as esters and analogs of ascorbic acid in cream such as ascorbyl palmitate, magnesium ascorbyl phosphate, ascorbyl methyl silanol and other ester and salt forms of ascorbic acid unfortunately can not be directly utilized by skin. It appears that the complex form must have contact with skin and then be converted to ascorbic acid by available cellular enzymes. This is a largely inefficient process for cosmetic and therapeutical purposes.

The present invention also relates to the usage of a composition for dermatological application which includes at least one water-sensitive pharmacologically active ingredient and at least one hydrophilic organic primary solvent to solubilize and stabilize the high content of active ingredient, such as L-Ascorbic acid. The composition can also contain at least one secondary hydrophilic solvent, a dermatologically acceptable polymer and other pharmaceutical or cosmetic adjuvants. The water-sensitive pharmacologically active agent used in this invention can be an enzyme, an antibotic or a vitamin. The enzyme could be protease, papain, subtilisin, catalase or cellulase. The water-sensitive or water-degradable pharmacologically active antibiotics used in this invention can be neomycin, bacitracin, tetracycline, erythromycin, clindamycin, or doxorubicin. The vitamin suitable for this invention can be L-Ascorbic acid, vitamin E or vitamin A.

The amount of a solid ingredient is usually expressed by its weight, and the amount of a liquid ingredient is usually expressed by its volume. The amount of a solid ingredient in the final liquid composition or formulation is usually expressed as the weight of the solid ingredient by volume of the final liquid composition (w/v). The amount of a liquid ingredient in the final liquid composition or formulation is usually expressed as the volume of the liquid ingredient by volume of the final liquid composition (v/v).

The quantity of water-degradable or water-sensitive pharmacologically active agent used in this invention depends upon the therapeutic or cosmetic purpose. Generally the quantity of these active agents is from the range of 0.1 to 50% by weight, preferably from 0.3 to 40% by weight, more preferably from 0.5 to 5 by weight of the final composition.

The hydrophilic non-polar primary solvent employed in this invention includes N-methyl-2-pyrrolidone ("NMP" Trade name: Pharmasolve, ISP), caprylyl pyrrolidone (Trade name: Surfacone LP-100, ISP), lauryl pyrrolidone (Trade name: Surfacone LP-300, ISP) and a combination of them, in any proportion range.

The hydrophilic non-polar secondary solvent employed in this invention includes dimethyl isosorbide (Trade name:Arasolve DMI, ICI), polyol (such as glycerin, or propylene glycol) and a combination thereof, in any proportion range.

The dermatological polymer employed in this invention includes hydroxypropylcellulose, hydroxylpropylmethylcellulose ("HPMC"), methylcellulose, and carboxylmethylcellulose from about 1 to about 6% range by weight.

The other pharmaceutical and/or cosmetic adjuvants usable in this invention includes conventionally available and acceptable materials for topical solution, gel, creams, ointments, and lotions from the range of about 0.1. to about 15% by weight.

The composition in this invention can be prepared in a particular dosage form such as a solution, a gel, a cream, an ointment and a lotion. These various topical dosage forms can be manufactured according to the usual process and method practiced in the pharmaceutical or cosmetic industry.

The following working formulations and processes as examples in this invention are for purposes of illustration only and are not intended to limit the scope of the claimed invention.

EXAMPLE 1

| | |
|---|---|
| L-Ascorbic Acid | 45 gm. |
| N-Methyl-2-Pyrrolidone (NMP) | up to 100 mL. |

Process: Ascorbic acid was dissolved in NMP with agitation in a suitable container until a clear almost colorless solution was obtained.

EXAMPLE 2

The formulation ingredients and process in this example were the same those as Example 1 except the quantity of the ascorbic acid was from the range of 1 gm to 44.9 gm.

EXAMPLE 3

| L-Ascorbic Acid | 35 gm. |
|---|---|
| Dimethyl Isosorbide (DMI) | 5 mL |
| NMP | up to 100 mL |

Process: Ascorbic acid was dissolved in about 50 mL of NMP with agitation in a suitable container and if necessary, more of NMP was added into the mixture but the total volume was kept under the 95 mL. After obtaining a clear solution, DMI was added with agitation into the solution and NMP was used to make the final volume to 100 mL. A homogeneous clear solution was obtained.

EXAMPLE 4

The formulation ingredients and process in this example were the same as Example 3, except the quantity of NMP and DMI were from the range of 35 to 49 mL and 6 to 20 mL, respectively.

EXAMPLE 5

| L-Ascorbic Acid | 30 gm. |
|---|---|
| Polyol | 5 mL |
| NMP | up to 100 mL. |

Process: Same as Example 3. The polyol in this example was glycerin, propylene glycol or a mixture thereof in any proportion range.

EXAMPLE 6

| L-Ascorbic Acid | 30 gm. |
|---|---|
| Mixture of DMI and Polyol | 5 mL |
| NMP | up to 100 mL. |

Process: Same as Example 3, except the mixture of DMI and polyol, in any proportion, was used to replace the DMI. The polyol was as recited in Example 5.

EXAMPLE 7

The formulation, ingredients and process in this example were the same as those of Example 3, except the quantity of ascorbic acid used was from the range of 1 to 34.9 gm.

EXAMPLE 8

The formulation ingredients and process in this example were the same as those of Example 4, except the quantity of ascorbic acid used was from the range of 1 to 34.9 gm.

EXAMPLE 9

The formulation ingredients and process in this example was the same as those of Example 5, except the quantity of ascorbic acid used was from the range of 1 to 29.9 gm.

EXAMPLE 10

The formulation ingredients and process in this example was the same as those of Example 6, except the quantity of ascorbic acid used was from the range of 1 to 29.9 gm.

EXAMPLE 11

| L-Ascorbic Acid | 45 gm. |
|---|---|
| Hydroxypropylmethylcellulose (HPMC) | 1 gm. |
| NMP | up to 100 gm. |

Process: Ascorbic acid was dissolved in a sufficient quantity of NMP. After obtaining a clear solution, HPMC was added with moderate agitation until a homogeneous gel was formed. Additional NMP was used to make up the final total weight.

EXAMPLE 12

The formulation, ingredients and process in this example were the same as those of
Example 11, except the quantity of ascorbic acid used was from the range of 1 to 44.9 gm.

EXAMPLE 13

| L-Ascorbic Acid | 35 gm |
|---|---|
| HPMC | 1 gm. |
| DMI | 5 mL |
| NMP | up to 100 gm. |

Process: Ascorbic acid was dissolved in about 50 mL of NMP with agitation and, if necessary, more of NMP was added into the mixture but the total volume was kept to less than 94 mL. After obtaining a clear solution, DMI and HPMC were added into the solution with moderate agitation until a homogeneous gel was obtained. The final weight to 100 gm. was obtained by adding NMP. After agitation the result was a homogeneous clear gel.

EXAMPLE 14

| L-Ascorbic Acid | 30 gm. |
|---|---|
| HPMC | 1 gm. |
| Mixture of DMI and Polyol | 5 mL |
| NMP | up to 100 mL. |

Process: Same as in Example 13, except the mixture of DMI and Polyol, in any proportion, was used instead of DMI. The polyol was as recited in Example 5.

EXAMPLE 15

The formulation ingredients and process in this example were the same as those of Example 13, except the quantity of ascorbic acid used was from the range of 1 to 34.9 gm.

EXAMPLE 16

The formulation ingredients and process in this example were the same as those of Example 14, except the quantity of ascorbic acid used was from the range of 1 to 29.9 gm.

EXAMPLE 17

The formulation ingredients and process in this example were the same as those of Example 1 to Example 16, except containing a 0.01 to 10% preferably 0.1 to 8% by weight of traditional cosmetical fragrance(s) to impart a pleasant smell to the product.

EXAMPLE 18

The formulation ingredients and process in this example were the same as those of Example 1 to Example 17, except containing a 1 to 10% total volume or weight of traditional pharmaceutical and/or cosmetic adjuvant(s) to present an attractive appearance of the product.

EXAMPLE 19

Stability of L-Ascorbic Acid Formulation

| Formulation | Loss In Potency[1] in % (Color Change)[2] | | | |
|---|---|---|---|---|
| | 2 Mo | 6 Mo | 12 Mo | 18 Mo |
| 30% L-Ascorbic Acid in NMP[3] | 1.1 (0) | 2.8 (0) | 3.5 (0) | 5.0 (0) |
| 30% L-Ascorbic Acid in NMP | 2.8 (0) | 4.9 (+) | 6.4 (+) | 9.2 (+) |
| 22% L-Ascorbic Acid in 5% DMI + NMP | | 1.8 (0) | 2.1 (0) | 3.4 (+) |
| 20% L-Ascorbic Acid in 10% Glycerin + NMP | 2.3 (0) | 3.6 (0) | 4.0 (+) | 6.2 (+) |
| 27% L-Ascorbic Acid in 10% H$_2$O + NMP | 5.7 (++) | 8.7 (++) | | |
| 24% L-Ascorbic Acid in 20% H$_2$O + NMP | 10.8 (++) | | | |
| 21% L-Ascorbic Acid in 30% H$_2$O + NMP | 12.1 (+++) | | | |
| 18% L-Ascorbic Acid in 40% H$_2$O + NMP | 12.8 (++++) | 14.5 (++++) | | |
| 20% L-Ascorbic Acid in 60% Lactic Acid + H$_2$O | 24.1 (+++++) | 30.1 (+++++) | | |
| Commercial Topical Vitamin C[3,4] | | | | 69.2 (+++++++) |

[1]Determined by a "miniaturized" assay method for L-Ascorbic Acid, page 130, USP 23/NF 18 (The United States Pharmacopeia/The National Formulary, January 1, 1995).
[2]0 denotes no noticeable color change. Intensity of color change is indicated by the number of +'s.
[3]Protected from light.
[4]The product claimed to have a 10% concentration of Vitamin C. The duration of 18 months ("Mo") was the time after receiving the product.

What is claimed is:

1. A topical, water-free composition comprising, based on the weight by volume of the composition:
   from 1% to about 35% of a pharmacologically active agent consisting of L-ascorbic acid;
   N-methyl-2-pyrrolidone; and
   wherein the topical, water-free composition is in the form of a solution, a gel, a cream, an ointment, or a lotion, and wherein the L-ascorbic acid in the composition does not lose more than 5% of its potency within two months at ambient storage conditions.

2. A topical, water-free composition comprising, based on the total weight of the composition:
   from 1% to about 35% of a pharmacologically active agent consisting of L-ascorbic acid;
   from about 45% to about 94% of N-methyl-2-pyrrolidone;
   from about 5% to about 20% of glycerin; and
   wherein the topical, water-free composition is in the form of a solution, a gel, a cream, an ointment, or a lotion, and wherein the L-ascorbic acid in the composition does not lose more than 5% of its potency within two months at ambient storage conditions.

3. A method for stabilizing from 1% to about 35%, based on weight by volume, of a pharmacologically active agent consisting of L-ascorbic acid in the absence of water to give a solution, a gel, a cream, an ointment, or a lotion of the L-ascorbic acid, comprising:
   dissolving the pharmacologically active agent consisting of L-ascorbic acid in a hydrophilic non-polar primary solvent selected from the group consisting of N-methyl-2-pyrrolidone, caprylyl pyrrolidone, lauryl pyrrolidone, and a mixture thereof, wherein the L-ascorbic acid in the gel, the cream, the ointment, or the lotion does not lose more than 5% of its potency within two months at ambient storage conditions.

4. The method of claim 3 further comprising adding a hydrophilic non-polar secondary solvent selected from the group consisting of dimethyl isosorbide, polyol, and a mixture thereof.

5. A topical, water-free composition comprising, based on the weight by volume of the topical:
   from 1% to about 40% of a pharmacologically active agent consisting of L-ascorbic acid; and
   a hydrophilic non-polar primary solvent, the hydrophilic non-polar primary solvent comprising N-methyl-2-pyrrolidone, caprylyl pyrrolidone, lauryl pyrrolidone, or a mixture thereof, wherein the topical, water-free composition is in the form of a solution, a gel, a cream, an ointment, or a lotion, and wherein the L-ascorbic acid in the composition does not lose more than 5% of its potency within two months at ambient storage conditions.

6. The topical, water-free composition of claim 5 further comprising a hydrophilic non-polar secondary solvent in an amount of from about 1% to about 30%.

7. The topical, water-free composition of claim 5 further comprising from about 0.5% to about 10% of a dermatological polymer, wherein the dermatological polymer comprises hydroxypropylcellulose, methyl cellulose, hydroxypropylmethyl-cellulose, carboxylmethylcellulose, or a mixture thereof.

8. The topical, water-free composition of claim 5 further comprising from about 0.1% to about 15% of a pharmaceutical or cosmetic adjuvant, wherein the pharmaceutical or cosmetic adjuvant comprises a preserving agent, an antioxidant, a chelating agent, a perfume, a filler, a screening agent, a sequestrant, an essential oil, a colorant, lipid vesicle, or a mixture thereof.

* * * * *